(12) United States Patent
Talley et al.

(10) Patent No.: US 7,301,624 B2
(45) Date of Patent: Nov. 27, 2007

(54) NANOSENSORS BASED ON FUNCTIONALIZED NANOPARTICLES AND SURFACE ENHANCED RAMAN SCATTERING

(75) Inventors: Chad E. Talley, Brentwood, CA (US); Thomas R. Huser, Livermore, CA (US); Christopher W. Hollars, Brentwood, CA (US); Stephen M. Lane, Oakland, CA (US); Joe H. Satcher, Jr., Patterson, CA (US); Bradley R. Hart, Brentwood, CA (US); Ted A. Laurence, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 333 days.

(21) Appl. No.: 10/935,783

(22) Filed: Sep. 7, 2004

(65) Prior Publication Data

US 2006/0050268 A1    Mar. 9, 2006

(51) Int. Cl.
*G01J 3/44*    (2006.01)
(52) U.S. Cl. ..................................... 356/301
(58) Field of Classification Search ................ 356/301, 356/73; 436/56; 977/920
See application file for complete search history.

(56) References Cited

U.S. PATENT DOCUMENTS

| | | | |
|---|---|---|---|
| 6,002,471 A * | 12/1999 | Quake | 356/73 |
| 6,149,868 A | 11/2000 | Natan et al. | |
| 6,242,264 B1 | 6/2001 | Natan et al. | |
| 6,344,272 B1 | 2/2002 | Oldenburg et al. | |
| 6,514,767 B1 | 2/2003 | Natan | |
| 2002/0142480 A1* | 10/2002 | Natan | 356/301 |
| 2003/0059820 A1 | 3/2003 | Vo-Dinh | |
| 2005/0027176 A1* | 2/2005 | Xie | 600/316 |
| 2005/0089901 A1* | 4/2005 | Porter et al. | 435/6 |
| 2005/0148100 A1* | 7/2005 | Su et al. | 436/523 |
| 2005/0221494 A1* | 10/2005 | Natan | 436/56 |
| 2006/0033910 A1* | 2/2006 | Sun et al. | 356/301 |

FOREIGN PATENT DOCUMENTS

| | | |
|---|---|---|
| WO | WO 01/33189 A2 | 5/2001 |
| WO | WO 03/010511 A2 | 2/2003 |

OTHER PUBLICATIONS

K. Kneipp, "Ultrasensitive Chemical Analysis by Raman Spectroscopy", 1999 American Chemical Society. Published on Web Sep. 28, 1999.

* cited by examiner

*Primary Examiner*—Gregory J. Toatley, Jr.
*Assistant Examiner*—Kara E Geisel
(74) *Attorney, Agent, or Firm*—Michael C. Staggs; John H. Lee

(57) ABSTRACT

Surface-Enhanced Raman Spectroscopy (SERS) is a vibrational spectroscopic technique that utilizes metal surfaces to provide enhanced signals of several orders of magnitude. When molecules of interest are attached to designed metal nanoparticles, a SERS signal is attainable with single molecule detection limits. This provides an ultrasensitive means of detecting the presence of molecules. By using selective chemistries, metal nanoparticles can be functionalized to provide a unique signal upon analyte binding. Moreover, by using measurement techniques, such as, ratiometric received SERS spectra, such metal nanoparticles can be used to monitor dynamic processes in addition to static binding events. Accordingly, such nanoparticles can be used as nanosensors for a wide range of chemicals in fluid, gaseous and solid form, environmental sensors for pH, ion concentration, temperature, etc., and biological sensors for proteins, DNA, RNA, etc.

48 Claims, 6 Drawing Sheets

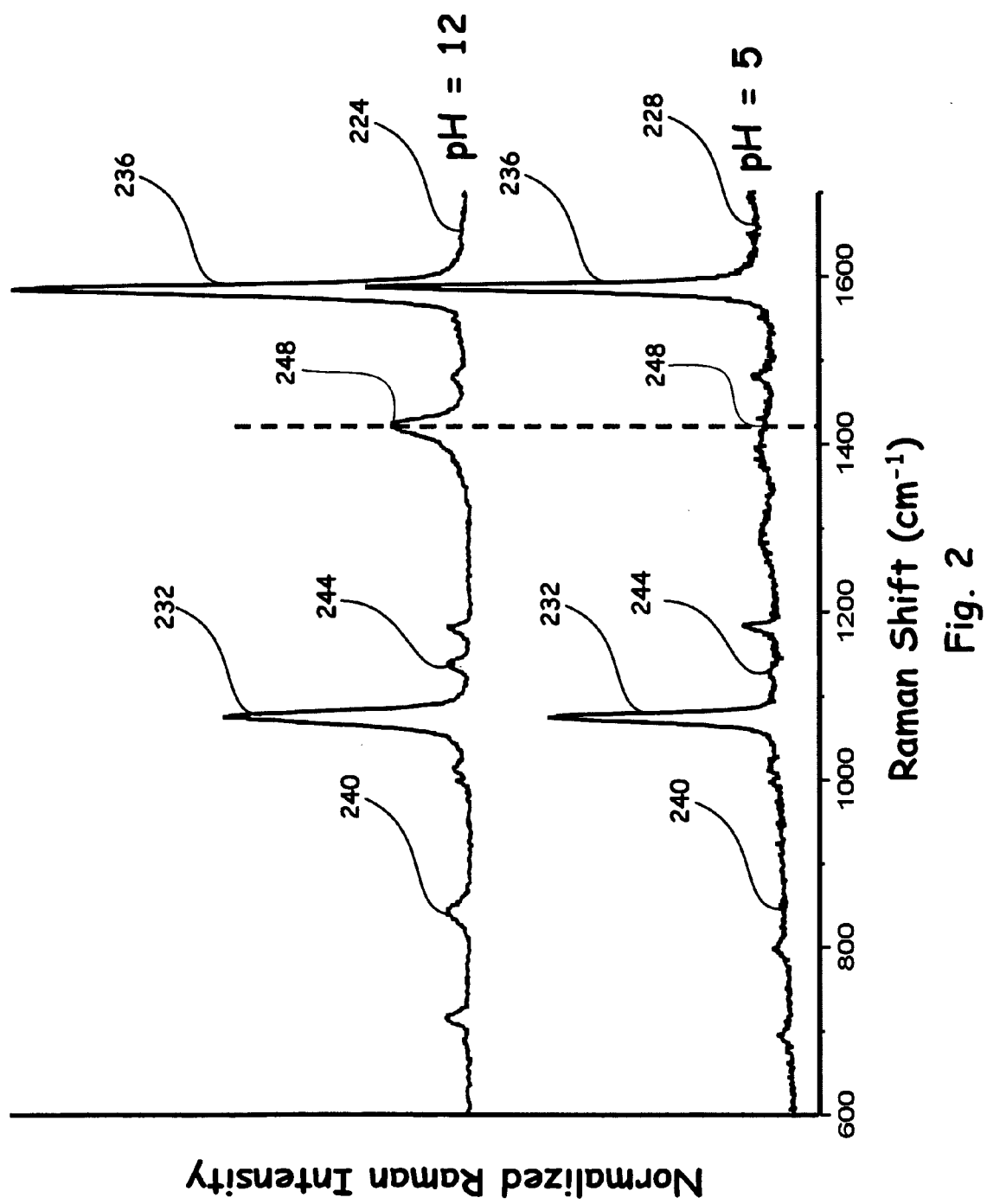

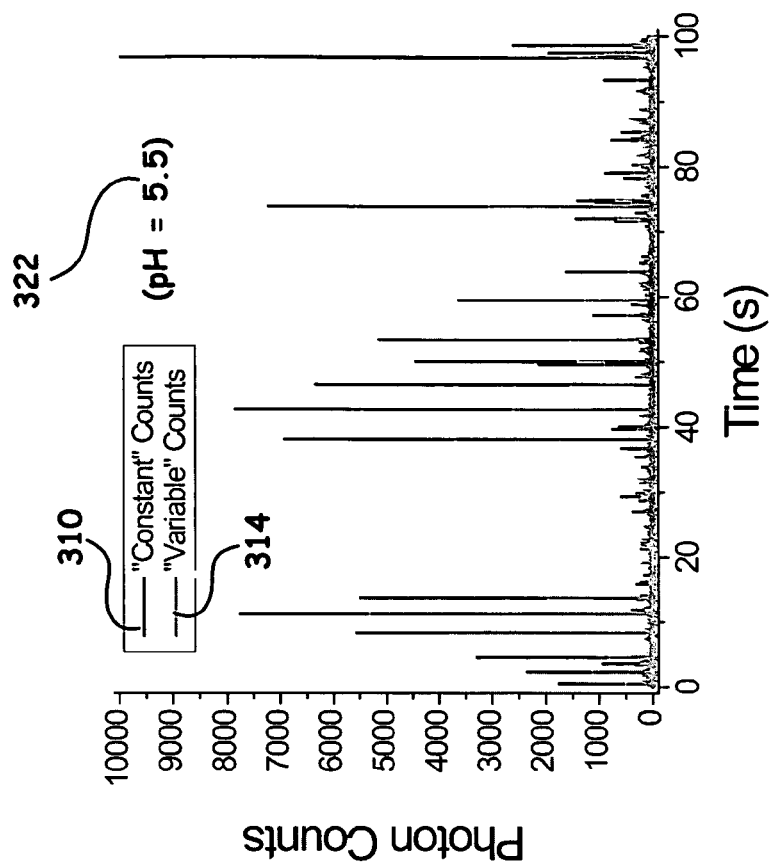
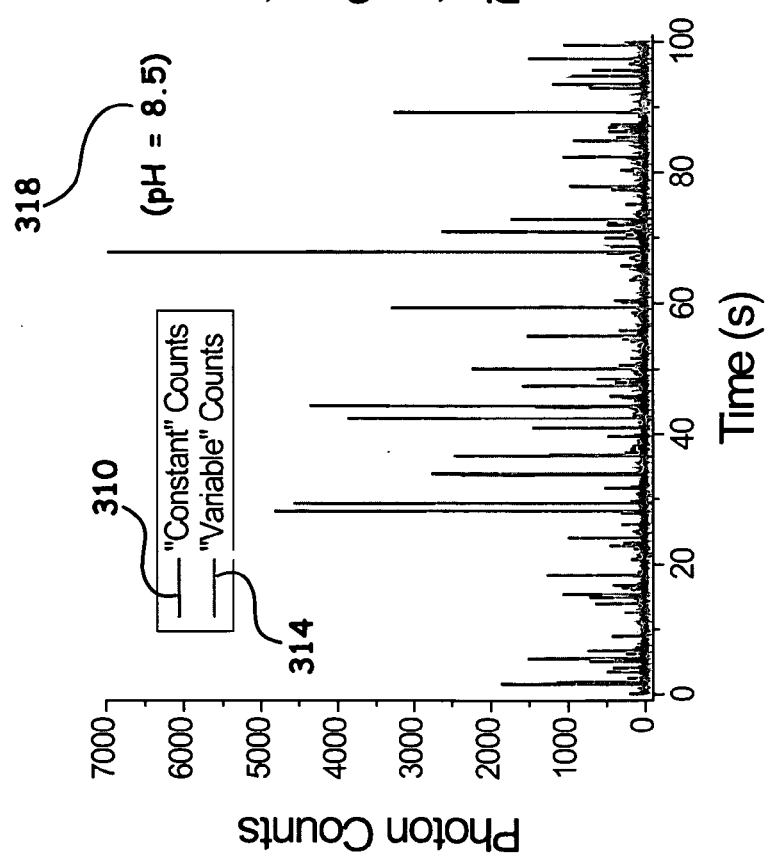
Fig. 3a
Fig. 3b

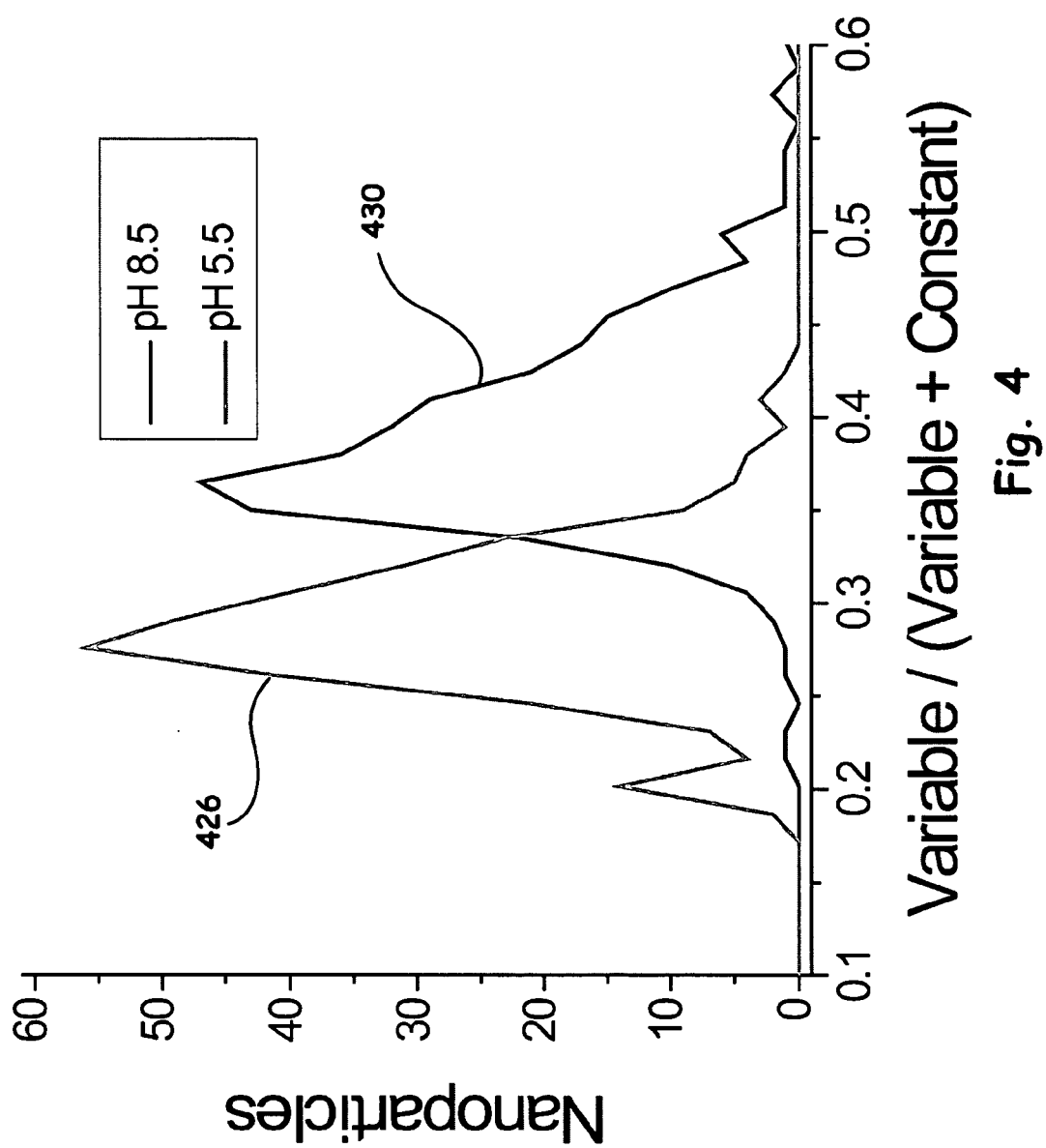

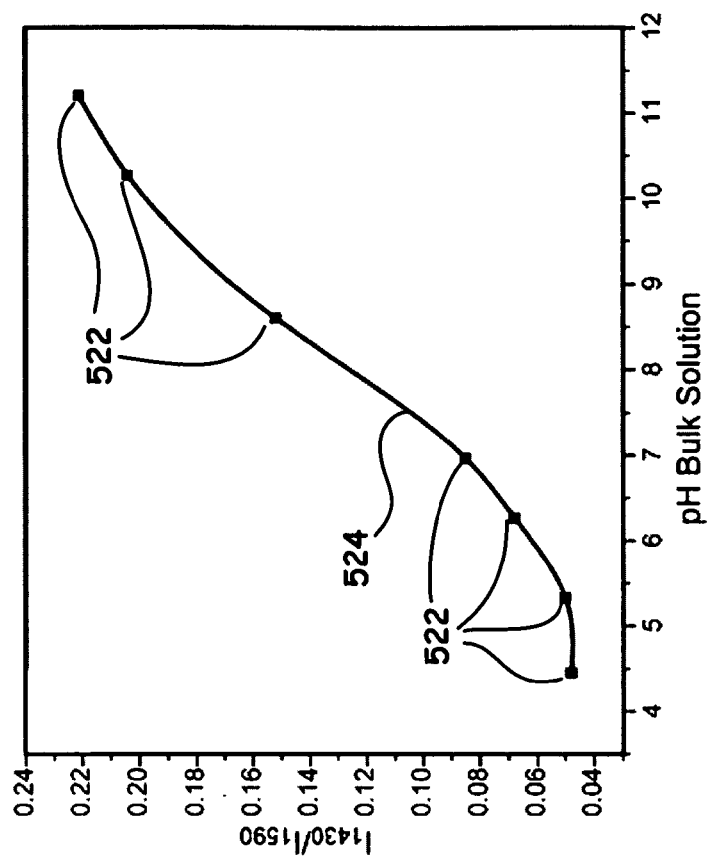
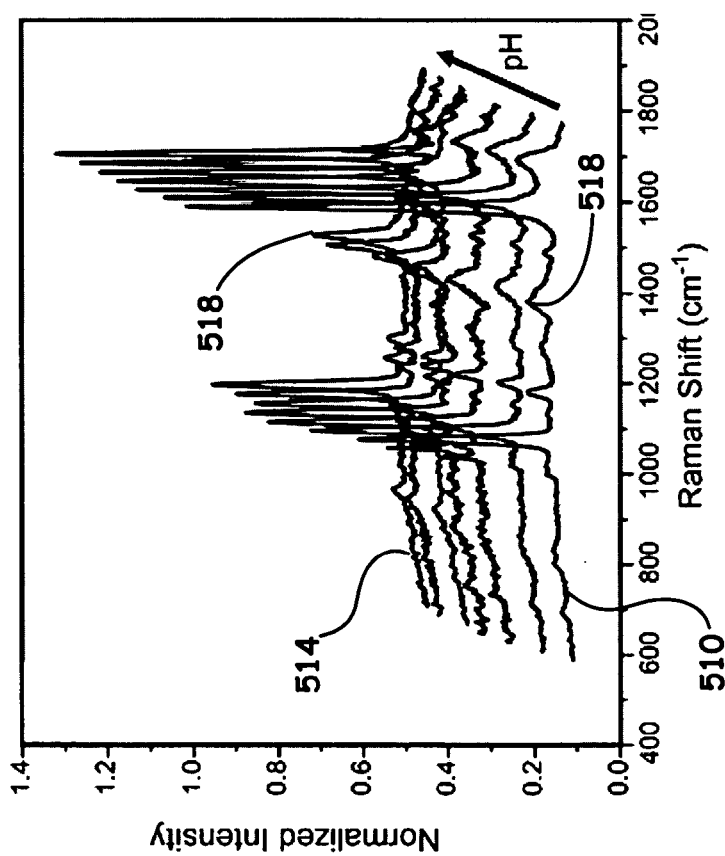
Fig. 5b
Fig. 5a

NANOSENSORS BASED ON FUNCTIONALIZED NANOPARTICLES AND SURFACE ENHANCED RAMAN SCATTERING

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates in general to molecular sensors and methods of identification, and more particularly to a nanosensor detection system for molecular identification based on surface-enhanced Raman scattering (SERS).

2. Description of Related Art

Raman scattering is the inelastic scattering of optical photons by interaction with vibrational modes of molecules. Typically, Raman scattered photons have energies that are slightly lower (i.e., Stokes-shifted photons) than the incident photons with the energy differences related to molecular vibrational energy levels. The energy spectrum of scattered photons commonly comprise narrow peaks and provides a unique spectral signature of the scattering molecule, allowing a molecule to be identified without the need for optical labels or prior knowledge of the chemicals present in the sample. Additionally, the vibrational spectra acquired in Raman spectroscopy are complementary to the vibrational spectra acquired by infrared (IR) absorption spectroscopy providing an additional database for peak assignment and molecular identification.

A drawback of Raman spectroscopy, however, is that the typical molecular cross-sections for Raman scattering are extremely low, on the order of $10^{-29}$ cm$^{-2}$. These low cross-sections often require high laser fluences and long signal integration times to produce spectra with sufficient signal-to-noise. While Raman spectroscopy has been used as an analytical tool for certain applications due to its excellent specificity for chemical group identification, its low sensitivity historically has limited its applications to highly concentrated samples. Background for such a method is described by Lewis, I. R. and H. G. M. Edwards in *Handbook of Raman Spectroscopy*, Practical Spectroscopy, ed., Vol. 28. 2001, Marcel Dekker, Inc.: New York, 1054.

Surface-enhanced Raman scattering (SERS) provides an enhancement in the Raman scattering signal by up to $10^6$ to $10^{10}$ for molecules adsorbed on microstructures of metal surfaces. Background for this concept is described in *Surface-Enhanced Spectroscopy*, by Moskovits, M., Rev. Mod. Phys., 57(3): p. 783-828 (1985). The enhancement is due to a microstructured metal surface scattering process which increases the intrinsically weak normal Raman Scattering due to a combination of several electromagnetic and chemical effects between the molecule adsorbed on the metal surface and the metal surface itself.

The enhancement is primarily due to enhancement of the local electromagnetic field in the proximity of the molecule resulting from plasmon excitation at the metal surface. [Moskovits, M., *Surface-Enhanced Spectroscopy*, Rev. Mod. Phys., 1985. 57(3): p. 783-828; Kneipp, K., et al., *Ultrasensitive Chemical Analysis by Raman Spectroscopy*, Chem. Rev., 1999.99: p. 2957-2975]. Although chemisorption is not essential, when it does occur there may be further enhancement of the Raman signal, since the formation of new chemical bonds and the consequent perturbation of adsorbate electronic energy levels can lead to a surface-induced resonance effect. [Moskovits, M., *Surface-Enhanced Spectroscopy*, Rev. Mod. Phys., 1985. 57(3): p. 783-828; Kneipp, K., et al., *Ultrasensitive Chemical Analysis by Raman Spectroscopy*, Chem. Rev., 1999. 99: p. 2957-2975]. The combination of surface- and resonance-enhancement (SERS) can occur when adsorbates have intense electronic absorption bands in the same spectral region as the metal surface plasmon resonance, yielding an overall enhancement as large as $10^{10}$ to $10^{12}$. Kneipp, K., et al., *Ultrasensitive Chemical Analysis by Raman Spectroscopy*, Chem. Rev., 1999. 99: p. 2957-2975.

In addition to roughened metal surfaces, solid gold and silver nano-particles in a size range of approximately 40 nm to about 200 nm can also generate SERS. These particles support resonant surface plasmons that can be excited by light in the visible part of the optical spectrum, wherein the absorption maximum for such particles depends on a number of factors, such as material (e.g., gold, silver, copper), size, shape and the dielectric constant of the medium surrounding the particle.

[Yguerabide, J. and E. E. Yguerabide, *Light-Scattering Submicroscopic Particles as Highly Fluorescent Analogs and Their Use as Tracer Labels in Clinical and Biological Applications, II. Experimental Characterization*. Anal. Biochem., 1998. 262: p. 157-176; Yguerabide, J. and E. E. Yguerabide, *Light-Scattering Submicroscopic Particles as Highly Fluorescent Analogs and Their Use as Tracer Labels in Clinical and Biological Applications, I. Theory*. Anal. Biochem., 1998. 262: p. 137-156]. These properties make the particles useful as substrates for surface-enhanced Raman spectroscopy, which can increase the Raman-scattered signal by many orders of magnitude above that of conventional SERS approaches involving planar, roughened surfaces. Kneipp, K., et al., *Ultrasensitive Chemical Analysis by Raman Spectroscopy*, Chem. Rev., 1999. 99: p. 2957-2975.

Typically, molecules adsorb to the particles by charge-interaction (electrostatics) with the charged particles, or by covalent binding through sulfur-containing chemical groups (e.g., thiol-groups). Additional improvement in signal-to-noise occurs because the conducting nanoparticles tend to quench any natural fluorescence produced by the molecules. These increases in Raman signal have been shown to be large enough to allow the Raman spectra from single molecules to be obtained. [Kneipp, K., et al., *Single Molecule Detection Using Surface-Enhanced Raman Scattering (SERS)*. Phys. Rev. Lett., 1997. 78(9): p. 1667-1670; Nie, S. and S. R. Emory, *Probing Single Molecules and Single Nanoparticles by Surface-Enhanced Raman Scattering*. Science, 1997. 275: p. 1102-1106]. This extraordinary increase in the Raman signal makes it possible to obtain Raman spectra rapidly and therefore makes it feasible to use Raman spectroscopy for real-time sensor applications.

Background information for systems and methods based on Raman and surface-enhanced Raman scattering (SERS) is described and claimed in U.S. Patent No. 2003/0059820 A1, entitled "SERS Diagnostic Platforms, Methods and Systems Microarrays, Biosensors and Biochips," issued Mar. 27, 2003 to Vo-Dinh, including the following, "In a preferred embodiment of the invention, the sampling platform is a SERS platform, permitting the system to be a SERS sensor. The SERS sampling platform includes one or more structured metal surfaces. A plurality of receptor probes are disposed anywhere within the range of the enhanced local field emanating from the structured metal surfaces. The Raman enhancement occurs upon irradiation of the structured metal surfaces. Such receptor probe proximity permits SERS enhancement of the Raman signal from the receptor probe/target combination which is formed following a binding event . . . ."

A need exists for an improved Surface-Enhanced Raman Spectroscopy (SERS) method and apparatus/system to determine the presence and concentration of one or more target molecules, and/or changing physical and/or chemical conditions of an analyte. The present invention is directed to such a need.

SUMMARY OF THE INVENTION

The present invention is directed to a surface-enhanced Raman spectroscopy (SERS) apparatus that utilizes designed nanosensors and detection means to determine the presence and concentration of one or more target molecules, and/or changing physical and/or chemical conditions of an analyte.

Another aspect of the present invention is directed to a surface-enhanced Raman spectroscopy (SERS) system having a directed electromagnetic radiation source, one or more nanosensors, optical detectors configured to monitor ratiometric signals of a collected SERS spectra coupled with means to determine the presence and concentration of one or more target molecules, and/or changing physical and/or chemical conditions of an analyte.

A final aspect of the present invention is directed to a SERS-based detection method that includes providing one or more nanosensors, each having a metal nanoparticle covalently bonded to one or more Raman-active molecules. By measuring ratiometric signals of a SERS spectra produced by the Raman-active molecules, the present invention can determine the presence and concentration of one or more target molecules, and/or changing physical and/or chemical conditions of an analyte from induced changes in a collected SERS spectra.

Accordingly, the present invention provides a desired surface-enhanced Raman spectroscopy (SERS) apparatus/system and method to determine the presence and concentration of one or more target molecules, and/or changing physical and/or chemical conditions of an analyte such as, for example, biological agents, industrial chemicals, toxins, poisons, glucose and pH monitoring, single cell nanosensors, etc. Such a system and method can be implemented in applications that include medicine, health care, biotechnology, environmental monitoring and national security.

BRIEF DESCRIPTION OF THE DRAWINGS

FIG. 2 shows SERS spectra of functionalized 4-MBA nanoparticles indicating pH sensitivity.

FIG. 3a shows photon counting pH 8.5 data as produced by the present invention.

FIG. 3b shows photon counting pH 5.5 data as produced by the present invention.

FIG. 4 shows ratio histograms of pH sensitive peaks and constant peaks.

FIG. 5a illustrates nanosensor response of the present invention as a function of pH.

FIG. 5b shows a normalized intensity plot versus the pH of the bulk solution for the carboxylate stretching mode at 1430 $cm^{-1}$.

DETAILED DESCRIPTION OF THE INVENTION

Referring now to the following detailed information, and to incorporated materials; a detailed description of the invention, including specific embodiments, is presented.

Unless otherwise indicated, numbers expressing quantities of ingredients, constituents, reaction conditions and so forth used in the specification and claims are to be understood as being modified by the term "about." Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical value, however, inherently contains certain errors necessarily resulting from the standard deviation found in their respective testing measurements.

General Description

The present invention provides an apparatus/system and method for monitoring changes in surface enhanced Raman spectra of molecules with a molecular weight of less than about 1000 atomic mass units that are operatively coupled (e.g., by covalence bonding) to a metal nanoparticle's surface. Such changes can be reversible (e.g., changes in the local environment, such as pH, temperature, etc.) or irreversible (e.g., high affinity interactions or covalent bond formation).

By utilizing such designed nanosensors (i.e., herein meaning Raman active molecules coupled to nanoparticles) with detection means as disclosed herein, the present invention can determine the presence and concentration of one or more target molecules, and/or changing physical and/or chemical conditions of an analyte. For example, the present invention can be utilized to monitor pH, temperature, or ion concentration properties, or the invention can be utilized as a chemical sensor to monitor gases, fluids, solids, etc., or the present invention can be utilized as a biological sensor for proteins, DNA, RNA, ions, metals, reactive oxygen species, etc.

Specific Description

Figure 1:
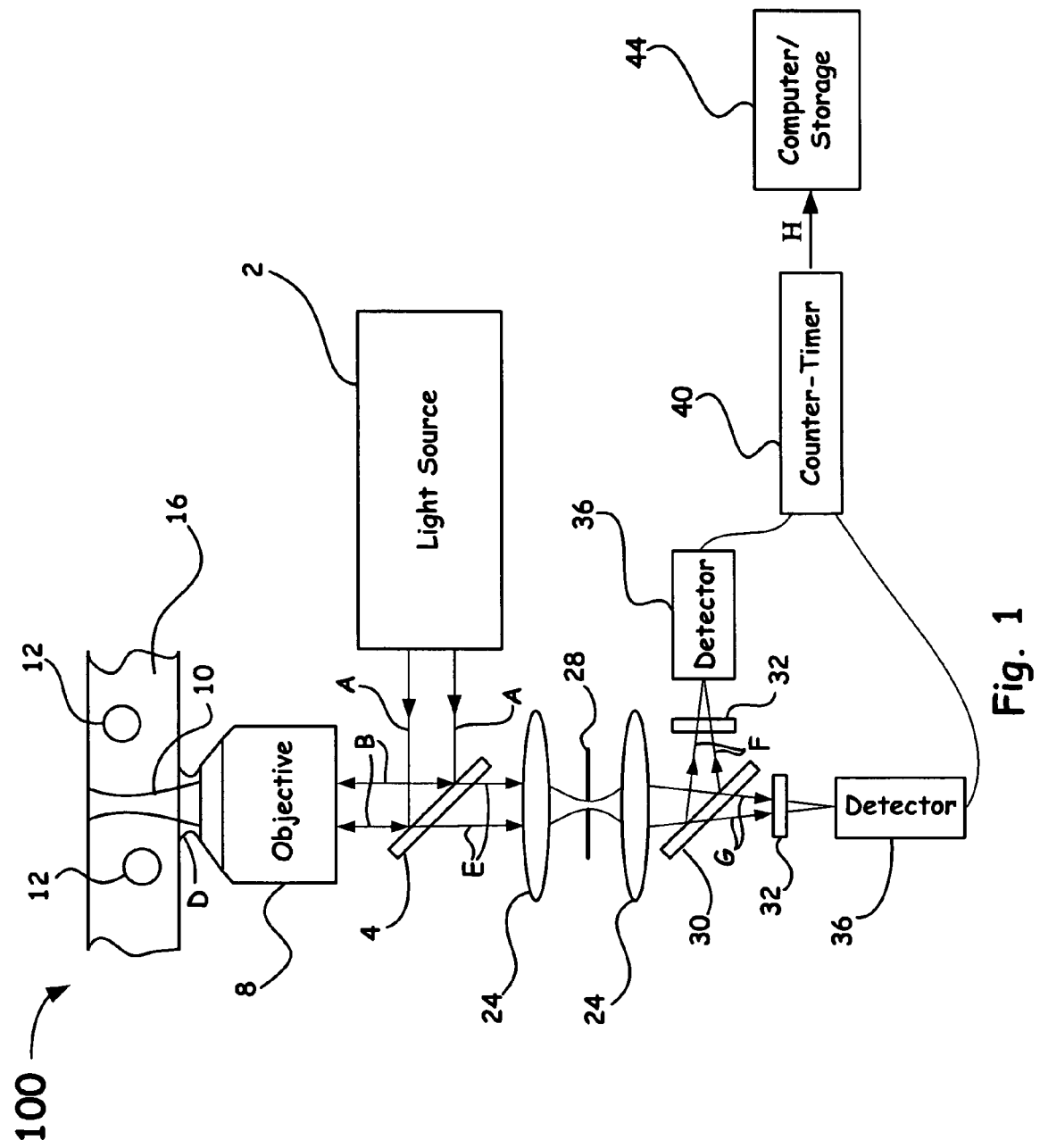
FIG. 1 illustrates a simplified schematic of the nanosensor system.

Turning now to the drawings, FIG. 1 shows a beneficial arrangement of a nanosensor system and is generally designated as reference numeral 100. Such an arrangement often can include electromagnetic radiation source 2, a mirror 4, such as a dichroic, an optical element 8, such as, but not limited to a microscope objective, one or more nanosensors 12 often disposed on a substrate (not shown), more often disposed within an aqueous solution 16, one or more optical elements 24 coupled with a pinhole 28, one or more beam directing elements 30, and one or more optical filters 32, such as edge filters, band-pass filters and/or notch filters to allow desired bands of electromagnetic radiation from source 2 to be monitored by detectors 36. Such monitored radiation can be directed to coupled electronics, such as, but not limited to, a counter-timer 40 when operating in a single photon counting mode and coupled electronically (denoted by H) to a computer 44 for further processing and analysis.

Electromagnetic radiation source 2, often a laser, is configured to output radiation along a path (denoted by the letter A with accompanying arrows, as shown in FIG. 1) and onto directing means, e.g., e-beam deposited beam-splitters, liquid crystal splitters, electro-optic devices, acousto-optic devices, mechanically driven reflective devices, and/or dichroic optics, such as mirror 4, having a known intensity and arranged with wavelengths between about 400 nm and about 1000 nm. Mirror 4 receives the radiation along beam path A, at a designed angle that depends on wavelength and reflectivity, often at 45°, and directs the radiation along the beam path denoted by the letter B. Additional directing means, such as optical element 8, arranged along beam path B, can be, for example, a diffractive optical component, such as a microscope objective operating in a confocal microscope configuration (e.g., operating with immersion oil as denoted by the letter D) to produce a beam spot 10 (e.g., a spot size defined within the Rayliegh range of element 8) having an intensity of often up to about 1 megawatt/cm$^2$. Such a desired intensity can be directed by optical element 8 to a designed area wherein one or more nanosensors 12 of the present invention are arranged randomly or as a regular array on a substrate (not shown) or disposed in a solution 16 for illumination upon crossing (e.g., diffusing) or positioning (e.g., by translation stages) into the region of beam spot 10.

Nanosensors 12 having individual nanoparticles and/or small clusters of nanoparticles as the sensor element are designed to scatter radiation facilitated by the excitation of plasmon modes produced on the surface of the nanoparticles. Element 8 can additionally operate as a means to collect scattered surface enhanced plasmon radiation and direct such surface enhanced plasmon radiation along path B through mirror 4 and along a path denoted by the letter E. The present invention can have optical diffractive elements 24 coupled with a pinhole 28 for rejecting out-of-focus light/beam homogenization and/or beam shaping and a predetermined filter, such as a notch filter (not shown) can be used to remove the Rayleigh scattered light (i.e., the scattered photons having the same energy as the incident photons illuminating nanosensors 12). The remaining SERS scattered light can be directed by additional one or more beam-directing means 30, such as, dichroic optics, e-beam deposited beam-splitters, liquid crystal splitters, electro-optic devices, acousto-optic devices, and/or mechanically driven reflective devices. By utilizing such beam-directing means 30, the one or more chemically sensitive modes and at least one other mode that is independent of the chemical environment can be directed along, for example, beam paths F and G in FIG. 1, through designed filters 32, such as, for example, narrow band-pass filters, edge filters, acousto-optic filters, etc., to select the Raman modes of interest. By selecting often two or more Raman modes of interest, more often just two modes, such an arrangement improves the speed of SERS detection by at least about two orders of magnitude by utilizing faster detectors, and by limiting the amount of data that is needed for storage and analysis. The remaining light can be focused onto one or more means for monitoring ratiometric signals 36, such as avalanche photodiodes operating in a single photon counting mode. While avalanche photodiodes are beneficial detectors of the present invention, other detectors operating as monitoring means, such as, but not limited to, CCD cameras (e.g., liquid nitrogen cooled CCD cameras, two-dimensional array detectors, avalanche CCD photodetectors), photomultipliers and/or a photodiodes, can be arranged to operate with the present invention without departing from the scope of the invention. Upon detection by means for monitoring ratiometric signals 36 and accumulated by a photon counter 40, SERS data can be processed by means 44, e.g., a computer, to store and manipulate detected SERS spectra.

Due to the highly localized effect of SERS, the nanosensors of the present invention include molecules having a molecular weight of less than about 1000 atomic mass units. Such nanosensors are often coupled by covalence bonding to metal nanoparticles such as gold, silver, copper and platinum, often having a size range from about 5 nm to about 1 μm, more often having a size range between 50 nm and about 100 nm. The predetermined molecules, having a desired functionality (i.e., for targeting specific chemicals, biological substances, etc.) are often attached to the nanoparticles using thiol chemistry to provide independent marker and reference modes and the specific functional modes. By having such nanosensors and by integrating such sensors with detection means, such as, but not limited to, spectrometers, microscopes (e.g., confocal configurations), photodiodes, CCD cameras, photomultipliers and/or a photodiodes capable of operating in a single photon counting mode, the present invention can detect the presence and concentration of one or more target molecules, and/or changing physical and/or chemical conditions of an analyte.

Nanoparticles as disclosed herein, which are coupled to the molecules, can be spherical, rodlike, cubic, triangular, ellipsoidal, or any variation of such shapes that are capable of supporting a plasmon resonance at an excitation wavelength between about 400 nm and about 1000 nm. Such nanoparticles can be attached to substrate surfaces as sensors or assays and they can be attached to such surfaces in random or regular arrays as single particles or nanoparticle clusters of functionlized nanoparticles. Each such cluster can be coated with a highly specific functional group for a different analyte such as, but not limited to, chemicals, DNA, RNA, proteins, etc. Such an array can be produced, for example, by inkjet-printing functionalized nanoparticles onto an inert surface or alternately by incorporating such nanoparticles into a supporting medium, such as an aerogel or polymer matrix.

As briefly discussed above, the example arrangement, as shown in FIG. 1, can be further arranged with additional apparatus, such as a compact laser source, such as a diode laser, and/or a spectrometer having a real-time monitoring detector, such as a charge couple device camera to aid in processing. Binding events to a functional group can be monitored by such a detector for color analysis of the colorimetric shift of the surface plasmon resonance of the nanoparticles while an atomic force microscope capable of being adapted with the invention, as shown in FIG. 1, can be utilized to image configured nanoparticles so as to aid in the analysis of resultant SERS spectra and/or response. In addition, functionalized nanoparticle clusters having functionality for a wider range of chemicals can be configured as nanosensors to monitor the binding of desired chemicals to a number of such clusters, e.g., binding to cluster 3 and 5 identifies chemical A, while binding to cluster 3, 5, and 8 identifies chemical B, etc. Moreover, as a further arrangement, such nanosensors of the present invention can be coupled to fiber optic cables for remote sensing.

Nanosensors of the present invention can also be unattached and free to move within an environment, such as being disposed in solution as shown in FIG. 1. By such an arrangement, functionalized nanoparticles of the present invention can be used to detect specific molecular species or can be configured for non-specific sensing applications by attaching to a range of or class of molecules. Moreover, such nanosensors as disclosed herein can be configured having "unfunctionalized" nanoparticles, i.e., they can be configured to detect molecules that attach to a nanoparticle's surface through a non-specific interaction, often by electrical charge interaction so as to monitor pH, charged biomolecules, charge clusters, and/or for ion sensing detection.

As an alternative, functionalized nanosensors can also be configured with a magnetic core and utilized as an active collector. By incorporating a magnetic core into the nanoparticles that make up the nanosensors as disclosed herein, they can be added to a solution of interest, such as shown in FIG. 1, and actively sorted by external magnetic fields and then extracted. The presence of molecules of interest can then be detected externally by, for example, a single particle flow cytometer, which can interrogate single particles in a flow stream to obtain a SERS spectrum of a functional group having any potentially bound molecules.

Industrial chemicals and chemicals that can be detected by the method and apparatus/system of the present invention include, but are not limited to, $NH_3$, $HNO_3$, NO, $N_2O$, Tributyl phosphate, Butyl nitrate, Butanol, Kerosene, Uranium nitrate hexahydrate, Acrolein, Isoprene, Butadiene, Alkyl iodides, Methyl hydrazine, Hydrazine, Methyl isocyanate, Methyl Mercaptan, Nitrogen Dioxide, Parathion, Phosgene, Phosphine, Sulfur Dioxide, Toluene diisocyanate, Allyl Alcohol, Acrolein, Acrylonitrile, Ammonia, Arsine, Chlorine, Diborane, Ethylene Oxide, Formaldehyde, Hydrogen Bromide, Hydrogen Cyanide, Hydrogen Selenide, and Hydrogen sulfide. Sensor molecules for the detection of such substances can include, but are not limited to, lanthanides, multi-dentate chelates (e.g., EDTA, etc.), nucleophilic groups, alcohols, lewis acids/bases, thiol-modified EDTA (for the detection of Uranium nitrate hexahydrate), or a Diels-Alder reactions (for the detection Butadiene).

Biological substances that can be detected include, but are not limited to, ions such as those used in signal transduction, metals (e.g., iron), reactive oxygen species, RNA, and DNA. Examples for SERS-sensing functional groups for the detection of such biological substances include, but are not limited to, thiol-modified chelates (e.g., EDTA) for the detection of metals, thiol-modified peptide sequences having sizes of up to about 20 nm for targeting desired epitopes in proteins, synthetic high-affinity ligands for proteins, and complimentary DNA sequences for the detection of DNA and RNA.

As a beneficial example application of the present invention, a SERS spectrum produced by nanosensors of individual nanoparticle clusters, such as, but not limited to silver nanoclusters, which are functionalized by adding, for example, a 30 μL aliquot of a 30 mM methanol solution of 4-mercaptobenzoic (hereafter 4-MBA) to an aqueous nanoparticle solution, can be utilized to respond to the pH changes of a surrounding medium in the range from about 6 to about 8, which makes such functionalized sensors amenable to biological systems.

FIG. 2 illustrates such a SERS spectra at a high 224 (pH of 12) and a low 228 (pH of 5) pH as measured by the example embodiment, as shown in FIG. 1, using 4-MBA functionalized nanoparticles as the nanosensors. The most prominent features in such spectra are ring breathing modes 1077 $cm^{-1}$ 232 and 1590 $cm^{-1}$ 236. Several vibrational modes which are less intense are also visible and show dependence in signal intensity on the pH of the surrounding solution. Such peaks have been assigned to a bending mode at 845 $cm^{-1}$ 240, a mixed mode at 1140 $cm^{-1}$ 244, and a stretching mode at 1430 $cm^{-1}$ 248 (as denoted along the dashed line).

For the measurement as shown in FIG. 2, stretching mode at 1430 $cm^{-1}$ 248 is monitored through optical filtering because such a mode shows the most intense of the Raman modes sensitive to the pH in the local environment surrounding the nanosensors. Ring breathing mode at 1077 $cm^{-1}$ 232 is optically filtered for monitoring as well so as to normalize photon counted measurements between the two spectra. However, although ring breathing modes 1077 $cm^{-1}$ 232 are chosen as a prominent peak for normalization, any predetermined pH insensitive peak within a given spectra, such as, for example, ring breathing modes 1590 $cm^{-1}$ 236, as shown in FIG. 2, can be used for normalization purposes. As illustrated in FIG. 2, the intensity of stretching mode at 1430 $cm^{-1}$ 248 is dependent on the pH in the local environment surrounding the nanosensors utilized in the present invention. Accordingly, as the pH is lowered (from a pH of 12 to a pH of 5 as shown by respective spectra 224 and 228) and the number of dissociated carboxylate groups decreases, the intensity of stretching mode at 1430 $cm^{-1}$ 248 decreases.

FIG. 3a shows photon counting data obtained by detectors 36, as shown in FIG. 1. Such data, shows constant 310 SERS signals, shown as dark lines (representative of pH prominent peak 232, as shown in FIG. 2), for normalization purposes plotted as a function of time along with variable 314 SERS signals, shown as lighter shaded lines (representative of pH sensitive peak 248, as shown in FIG. 2) of the MBA coated nanosensors disposed within a pH of 8.5 318.

FIG. 3b shows photon counting data obtained by detectors 36, as shown in FIG. 1. Such data, shows constant 310 SERS signals, shown as dark lines (representative of pH prominent peak 232, as shown in FIG. 2), for normalization purposes plotted as a function of time along with variable 314 SERS signals, shown as lighter shaded lines (representative of pH sensitive peak 248, as shown in FIG. 2) of the MBA coated nanosensors disposed within a pH of 5.5 322.

FIG. 4 shows histograms of the ratio between the pH sensitive peak (i.e., stretching mode at 1430 $cm^{-1}$ 248, as shown in FIG. 2) and the constant peak (i.e., prominent peak 232, as shown in FIG. 2) used to normalize the signal for particle to particle variations. Accordingly FIG. 4 shows a pH of 5.5 ratio 426 and a pH of 8.5 ratio 430 of such peaks and illustrates that the intensity of the stretching mode at 1430 $cm^{-1}$ (248 as shown in FIG. 2) is dependent on the pH in the local environment surrounding such nanosensors.

FIG. 5a and FIG. 5b further illustrate nanosensor response of the present invention as a function of pH. For the resultant plot as shown in FIG. 5a, an immobilized nanosensor is positioned in a focused laser beam, such as shown in FIG. 1, and is interrogated spectroscopically while the pH is varied from 4.4 510 to 11.2 514. FIG. 5a demonstrates that as the pH increases from 4.4 510 to 11.2 514, the intensity of a stretching mode at 1430 $cm^{-1}$ 518 varies correspondingly. FIG. 5b further demonstrates the response sensitivity to pH by plotting individual data points 522 for the carboxylate stretching mode at 1430 $cm^{-1}$ along normalized intensity versus bulk solution pH coordinates. A line 524 connecting the data points is added as a visual guide.

Moreover, by utilizing individual nanoparticles and/or small nanoclusters (e.g., nanoparticles and/or clusters having dimensions between about 5 nm and 1 μm more often between about 50 nm and 100 nm), such nanoparticles and/or nanoclusters can also be arranged as sensors inside single living cells. Such sizes of the nanoparticles and/or clusters combined with the highly localized probe volume inherent to SERS make such resultant nanosensors particularly beneficial for monitoring biological processes in vivo. Functionalized nanoparticles to be used as a probe can be micro-injected into cells or the cells can be forced to take nanoparticles up passively (e.g., phagocytosis) or by ultra-sonification and/or electroporation of the cells and/or by embedding the particles in liposomes or similar vesicles and/or by directed uptake, such as via lipid vesicles or by coating the particles with a peptide or other molecules that will cause them to be taken up by cells. Such a beneficial arrangement can be used to map intra and inter-cellular distributions of components such as, but not limited to proteins, DNA, RNA, glucose, calcium, pH, etc., with applications including in vivo or ex vivo blood type monitoring, tumor or lesion optical marking, and/or characterizing bacterial cells and/or their endospores.

Figures 6A, 6B:
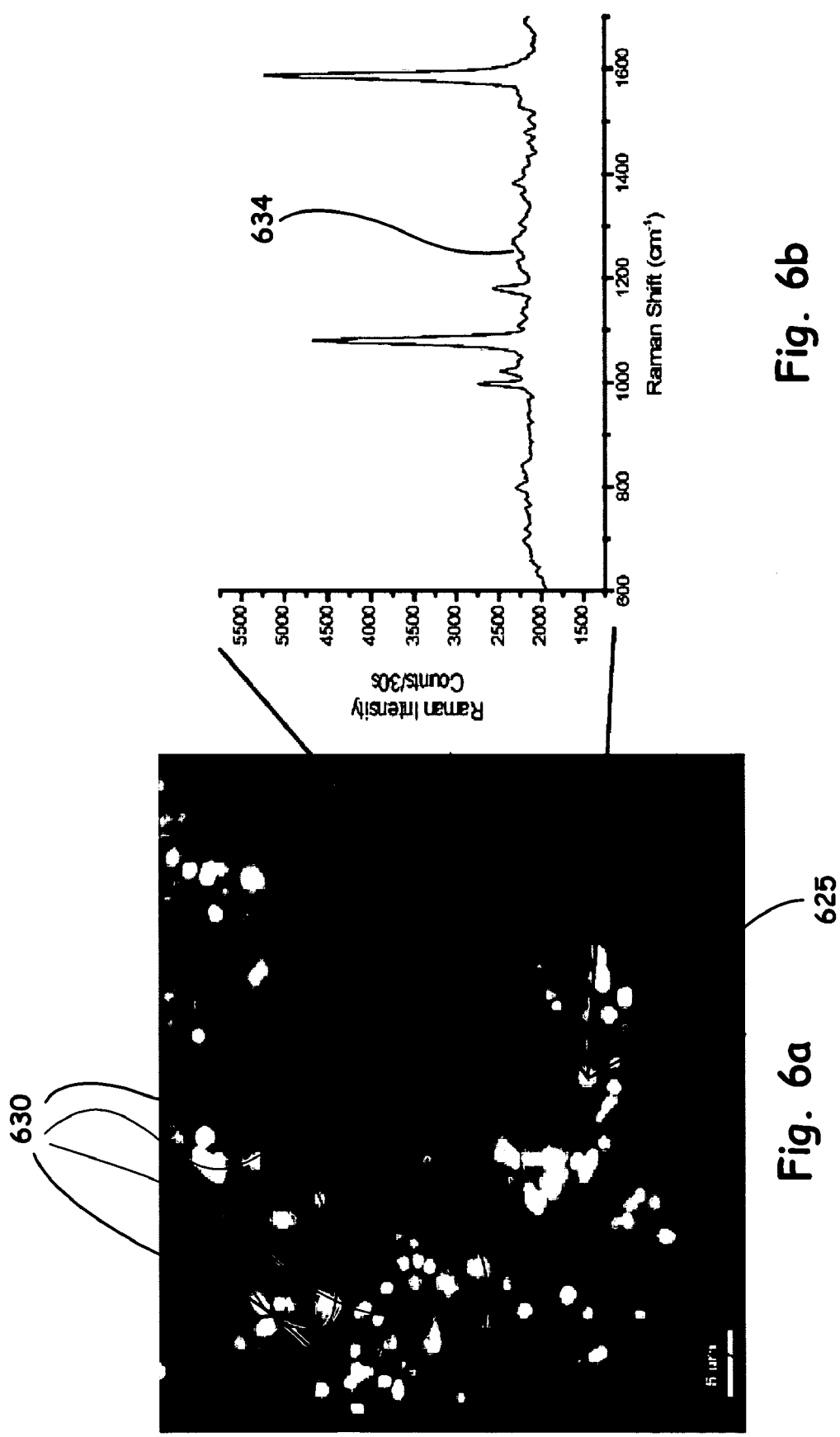
FIG. 6a shows an atomic force microscope image of Chinese Hamster Ovary Cells (CHO) after passive uptake of functionalized nanoparticles.
FIG. 6b shows a CHO cell SERS spectra characterisitic of p-mercaptobenzoic acid.

FIG. 6a and FIG. 6b illustrate passive uptake of nanosensors having functionalized nanoparticles by Chinese Hamster Ovary cells (CHO). FIG. 6a shows a confocal microscope image produced by the present invention of a plurality of CHO cells e.g., 625 (others shown as bright areas within encircled regions 630) after incubation for 24 hours with 4-MBA coated silver nanoparticles. FIG. 6b shows a SERS spectra 634 representative of 4-MBA obtained from a nanosensor in a CHO cell 625. Accordingly, the resultant spectra illustrates that there is no interference when nanosensors of the present invention are incorporated into a biological environment, such as, but not limited to CHO cells.

Changes and modifications in the specifically described embodiments can be carried out without departing from the scope of the invention, which is intended to be limited by the scope of the appended claims.

The invention claimed is:

1. A SERS apparatus, comprising:
one or more nanosensors, each said nanosensor having one or more Raman-active molecules directly coupled to a metal nanoparticle and configured to produce a SERS spectra; and
a plurality of means for monitoring two or more specific molecular vibration signals of said SERS spectra, wherein said two or more specific molecular vibration signals comprise one or more monitored sensitive peaks that are changing relative to monitored predetermined one or more normalization peak signals, the resultant ratios utilized to determine the presence and concentration of one or more target molecules, and/or changing physical and/or chemical conditions of an analyte.

2. The apparatus of claim 1, wherein said monitoring means further comprises single photon counting.

3. The apparatus of claim 1, wherein said nanosensors are incorporated into one or more living cells to monitor changes in said cells comprising: pH, glucose, $CO_2$, reactive oxygen species, proteins, RNA and DNA.

4. The apparatus of claim 3, wherein said nanosensors are incorporated using micro-injection, passive uptake, directed uptake, ultra-sonification, electroporation, embedding in liposomes, embedding in vesicles similar to liposomes, and/or by coating said nanosensors with a peptide that will cause them to be taken up by said cells.

5. The apparatus of claim 1, wherein said one or more target molecules comprises at least one chemical selected from $NH_3$, $HNO_3$, NO, $N_2O$, Tributyl phosphate, Butyl nitrate, Butanol, Kerosene, Uranium nitrate hexahydrate, Acrolein, Isoprene, Butadione, Alkyl iodides, Methyl hydrazine, Hydrazine, Methyl isocyanate, Methyl Mercaptan, Nitrogen Dioxide, Parathion, Phosgene, Phosphine, Sulfur Dioxide, Toluene diisocyanate, Allyl Alcohol, Acrolein, Acrylonitrile, Ammonia, Arsine, Chlorine, Diborane, Ethylene Oxide, Formaldehyde, Hydrogen Bromide, Hydrogen Cyanide, Hydrogen Selenide, and Hydrogen sulfide.

6. The apparatus of claim 1, wherein said at least one Raman-active molecule is functionalized.

7. The apparatus of claim 6, wherein said one or more target molecules couple to said at least one Raman-active molecule by electrical charge interaction.

8. The apparatus of claim 1, wherein said metal nanoparticle has a size range between about 5 nm and about 1 μm.

9. The apparatus of claim 1, wherein said metal nanoparticle further comprises a magnetic core.

10. The apparatus of claim 1, wherein said one or more nanosensors are configured on a substrate.

11. The apparatus of claim 10, wherein said one or more nanosensors are arranged as an array.

12. The apparatus of claim 1, wherein said one or more nanosensors are disposed in solution.

13. The apparatus of claim 1, wherein said nanosensors are illuminated by an electromagnetic radiation source to produce said SERS spectra.

14. The apparatus of claim 13, wherein said electromagnetic radiation source includes a laser having a wavelength between about 400 nm and about 1000 nm.

15. The apparatus of claim 1, wherein said apparatus further comprises a spectrometer.

16. The apparatus of claim 1, wherein said apparatus further comprises an atomic force microscope.

17. A SERS system, comprising:
one or more nanosensors, each said nanosensor having one or more Raman-active molecules directly coupled to a metal nanoparticle;
an electromagnetic radiation source;
means configured to direct radiation from said electromagnetic radiation source onto disposed said one or more nanosensors and additionally configured to collect a SERS spectra resulting from said directed electromagnetic radiation source;
two or more optical detectors configured to monitor two or more specific molecular vibration signals of said SERS spectra, wherein said two or more specific molecular vibration signals provide for ratiometric signals comprising one or more monitored sensitive peaks that are changing relative to monitored predetermined one or more normalization peak signals; and
means to determine the presence and concentration of one or more target molecules, and/or changing physical and/or chemical conditions of an analyte resulting from the monitored ratiometric signals.

18. The system of claim 17, wherein said determination means further comprises single photon counting.

19. The system of claim 17, wherein said nanosensors are incorporated into one or more living cells to monitor changes in said cells comprising: pH, glucose, $CO_2$, reactive oxygen species, proteins, RNA and DNA.

20. The system of claim 19, wherein said nanosensors are incorporated using micro-injection, passive uptake, directed uptake, ultra-sonification, electroporation, embedding in liposomes, embedding in vesicles similar to liposomes, and/or by coating said nanosensors with a peptide that will cause them to be taken up by said cells.

21. The system of claim 17, wherein said one or more target molecules comprises at least one chemical selected from $NH_3$, $HNO_3$, NO, $N_2O$, Tributyl phosphate, Butyl nitrate, Butanol, Kerosene, Uranium nitrate hexahydrate, Acrolein, Isoprene, Butadione, Alkyl iodides, Methyl hydrazine, Hydrazine, Methyl isocyanate, Methyl Mercaptan, Nitrogen Dioxide, Parathion, Phosgene, Phosphine, Sulfur Dioxide, Toluene diisocyanate, Allyl Alcohol, Acrolein, Acrylonitrile, Ammonia, Arsine, Chlorine, Diborane, Ethylene Oxide, Formaldehyde, Hydrogen Bromide, Hydrogen Cyanide, Hydrogen Selenide, and Hydrogen sulfide.

22. The system of claim 17, wherein said at least one Raman-active molecule is functionalized.

23. The system of claim 22, wherein said one or more target molecules couple to said at least one Raman-active molecule by electrical charge interaction.

24. The system of claim 17, wherein said metal nanoparticle has a size range between about 5 nm and about 1 μm.

25. The system of claim 17, wherein said metal nanoparticle further comprises a magnetic core.

26. The apparatus of claim 17, wherein said one or more nanosensors are configured on a substrate.

27. The apparatus of claim 26, wherein said one or more nanaprobes are arranged as an array.

28. The system of claim 17, wherein said one or more nanosensors are disposed in solution.

29. The system of claim 17, wherein said nanosensors are illuminated by an electromagnetic radiation source to produce said SERS spectra.

30. The system of claim 29, wherein said electromagnetic radiation source includes a laser having a wavelength between about 400 nm and about 1000 nm.

31. The system of claim 17, wherein said system further comprises a spectrometer.

32. The system of claim 17, wherein said system further comprises an atomic force microscope.

33. A SERS-based detection method, comprising:
providing one or more nanosensors, each said nanosensor having a metal nanoparticle directly coupled to one or more Raman-active molecules;
measuring ratiometric signals of a SERS spectra produced by said one or more Raman-active molecules, wherein said ratiometric signals further comprise one or more monitored sensitive peaks that are changing relative to monitored predetermined one or more normalization peak signals in order to determine the presence and concentration of one or more target molecules, and/or changing physical and/or chemical conditions of an analyte from induced changes in said SERS spectra.

34. The method of claim 33, wherein said measuring step further comprises single photon counting.

35. The method of claim 33, wherein said one or more nanosensors are incorporated into one or more living cells to monitor changes in said cells comprising: pH, glucose, $CO_2$, reactive oxygen species, proteins, RNA and DNA.

36. The method of claim 33, wherein said nanosensors are incorporated using micro-injection, passive uptake, directed uptake, ultra-sonification, electroporation, embedding in liposomes, embedding in vesicles similar to liposomes, and/or by coating said nanosensors with a peptide that will cause them to be taken up by said cells.

37. The method of claim 33, wherein said one or more target molecules comprises at least one chemical selected from $NH_3$, $HNO_3$, NO, $N_2O$, Tributyl phosphate, Butyl nitrate, Butanol, Kerosene, Uranium nitrate hexahydrate, Acrolein, Isoprene, Butadione, Alkyl iodides, Methyl hydrazine, Hydrazine, Methyl isocyanate, Methyl Mercaptan, Nitrogen Dioxide, Parathion, Phosgene, Phosphine, Sulfur Dioxide, Toluene diisocyanate, Allyl Alcohol, Acrolein, Acrylonitrile, Ammonia, Arsine, Chlorine, Diborane, Ethylene Oxide, Formaldehyde, Hydrogen Bromide, Hydrogen Cyanide, Hydrogen Selenide, and Hydrogen sulfide.

38. The method of claim 33, wherein said at least one Raman-active molecule is functionalized.

39. The method of claim 38, wherein said one or more target molecules couple to said at least one Raman-active molecule by electrical charge interaction.

40. The method of claim 33, wherein said metal nanoparticle has a size range between about 5 nm and about 1 μm.

41. The method of claim 33, wherein said metal nanoparticle further comprises a magnetic core.

42. The method of claim 33, wherein said one or more nanosensors are configured on a substrate.

43. The method of claim 42, wherein said one or more nanosensors are arranged as an array.

44. The method of claim 33, wherein said one or more nanosensors are disposed in solution.

45. The method of claim 33, wherein said nanosensors are illuminated by an electromagnetic radiation source to produce said SERS spectra.

46. The method of claim 45, wherein said electromagnetic radiation source includes a laser having a wavelength between about 400 nm and about 1000 nm.

47. The method of claim 33, further comprising a spectrometer to analyze said SERS spectra.

48. The method of claim 33, further comprising monitoring means to collect ratiometric signals of said SERS spectra.

* * * * *